United States Patent
Borgos et al.

(10) Patent No.: US 10,244,978 B2
(45) Date of Patent: Apr. 2, 2019

(54) METHOD FOR ASSESSMENT OF CEREBROVASCULAR REGULATION

(71) Applicants: John A. Borgos, Shoreview, MN (US); Isabelle Richmond, Melbourne, FL (US)

(72) Inventors: John A. Borgos, Shoreview, MN (US); Isabelle Richmond, Melbourne, FL (US)

(73) Assignee: Brain Check Medical, LLC, Shoreview, MN (US)

(*) Notice: Subject to any disclaimer, the term of this patent is extended or adjusted under 35 U.S.C. 154(b) by 342 days.

(21) Appl. No.: 15/191,738

(22) Filed: Jun. 24, 2016

(65) Prior Publication Data

US 2017/0105671 A1    Apr. 20, 2017

Related U.S. Application Data

(60) Provisional application No. 62/285,054, filed on Oct. 19, 2015.

(51) Int. Cl.
*A61B 5/00* (2006.01)
*A61B 5/02* (2006.01)
(Continued)

(52) U.S. Cl.
CPC ........ *A61B 5/4076* (2013.01); *A61B 5/02028* (2013.01); *A61B 5/0261* (2013.01);
(Continued)

(58) Field of Classification Search
CPC ... A61B 5/021; A61B 5/14551; A61B 5/1046; A61B 2/0205; A61B 5/0075;
(Continued)

(56) References Cited

U.S. PATENT DOCUMENTS 6,616,613 B1    9/2003   Goodman
7,998,075 B2    8/2011   Ragauskas et al.
(Continued)

OTHER PUBLICATIONS

Steinmeier et al., "Slow Rhythmic Oscillations of Blood Pressure, Intracranial Pressure, Microcirculation, and Cerebral Oxygenation: Dynamic Interrelation and Time Course in Humans", Stroke. 1996; 27:2236-2243.*

(Continued)

*Primary Examiner* — Eric Winakur
*Assistant Examiner* — Chu Chuan (JJ) Liu
(74) *Attorney, Agent, or Firm* — Tysver Beck Evans, PLLC

(57) ABSTRACT

A system device and method are presented for determining if cerebral blood flow autoregulation functionality has been compromised in a patient. The system includes sensors for detecting and measuring at least two physiological parameters such as oxygenation and blood pressure. The system analyzes these measurements and presents them as waveforms. Episodes of interest in each waveform are determined and compared. Any time lag between the occurrence of episodes of interest in each waveform is established and accounted for. Where there is correspondence between episodes of interest in each waveform then impairment of cerebral blood flow autoregulation is likely.

10 Claims, 7 Drawing Sheets

(51) Int. Cl.
*A61B 5/026* (2006.01)
*A61B 5/03* (2006.01)
*A61B 5/1455* (2006.01)
*A61B 5/021* (2006.01)

(52) U.S. Cl.
CPC .......... *A61B 5/02108* (2013.01); *A61B 5/031* (2013.01); *A61B 5/14553* (2013.01); *A61B 5/6803* (2013.01); *A61B 5/6814* (2013.01); *A61B 5/4064* (2013.01)

(58) Field of Classification Search
CPC .............. A61B 5/0261; A61B 5/02028; A61B 5/14552; A61B 5/14553; A61B 5/031; A61B 5/4064; A61B 5/6803; A61B 5/6814; A61B 5/4076; A61B 5/1455; A61B 5/02108
See application file for complete search history.

(56) References Cited

U.S. PATENT DOCUMENTS

| | | | |
|---|---|---|---|
| 8,062,224 | B2 | 11/2011 | Ragauskas et al. |
| 8,088,074 | B2 | 1/2012 | Baruch et al. |
| 8,556,811 | B2 | 10/2013 | Brady |
| 2007/0027393 | A1* | 2/2007 | Williams ........... A61B 5/02156 600/485 |
| 2014/0073888 | A1 | 3/2014 | Sethi et al. |
| 2014/0296669 | A1* | 10/2014 | Gertsch ................ A61B 5/6803 600/324 |
| 2016/0106372 | A1 | 4/2016 | Addison et al. |
| 2017/0000395 | A1 | 1/2017 | Addison et al. |
| 2017/0000423 | A1 | 1/2017 | Addison et al. |

OTHER PUBLICATIONS

Sundgreen et al., "Autoregulation of Cerebral Blood Flow in Patients Resuscitated From Cardiac Arrest", Stroke. 2001; 32:128-132.*

Moerman et al., ("Assessment of Cerebral Autoregulation Patterns with Near-infrared Spectroscopy during Pharmacological-induced Pressure Changes", Anesthesiology 2015; 123:327-35.*

Nov. 21, 2016 PCT Search Report (Serial No. PCT/US16/51430)—Our Matter 5493.

Brady et al., Continuous Time-Domain Analysis of Cerebrovascular Autoregulation Using Near-Infrared Spectroscopy, http://stroke.ahajournals.org.

Hamner et al., Relative Contributions of Sympathetic, Cholinergic, and Myogenic Mechanisms to Cerebral Autoregulation, http://stroke.ahajournals.org.

Lane, Nick, PhD.; Seven Point Four; 2007.

Marmarelis et al., Linear and Nonlinear Modeling of Cerebral Flow Autoregulation Using Principal Dynamic Modes, The Open Biomedical Engineering Journal, 2012, 6, p. 42-55.

Panerai et al., Effect of CO2 on Dynamic Cerebral Autoregulation Measurement, Physiol. Meas. 20 (1999) IOP Publishing Ltd.

* cited by examiner

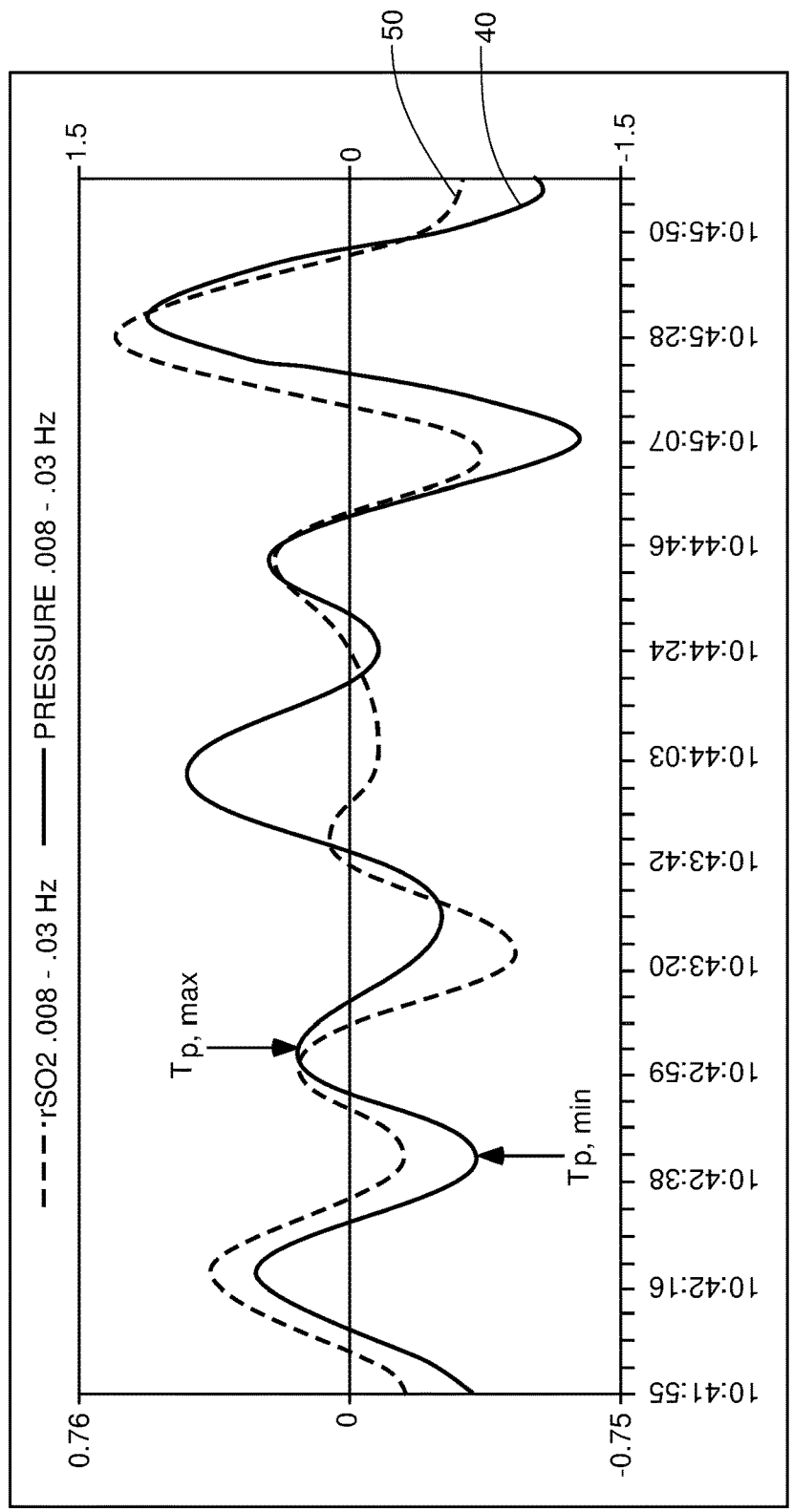

METHOD FOR ASSESSMENT OF CEREBROVASCULAR REGULATION

FIELD OF THE INVENTION

This disclosure is directed to methods, systems and apparatuses for the monitoring and assessment of cerebrovascular autoregulation of a patient.

BACKGROUND AND SUMMARY

Cerebral autoregulation (CAR) is a term commonly used to describe the pressure autoregulation mechanism that adjusts cerebrovascular resistance (tone) in response to blood pressure changes. It is thought that this mechanism acts to maintain adequate cerebral blood flow (CBF) over a wide range of arterial blood pressure in healthy subjects.

Various Cerebral autoregulatory mechanisms, including CAR, are influenced by various processes that operate on independent timescales. Studies have provided support for the belief that autonomic (neurogenic) control of cerebral vasculature is a primary factor in maintaining homeostatic cerebral blood flow, specifically in the arterial blood pressure range where cerebrovascular control mechanisms are most active in healthy individuals. These studies have also provided support for the belief that dysfunction of neurogenic control in individuals with mild or concussive brain injury could be responsible for clinical symptoms and the known risks of subsequent traumatic injury, even when arterial blood pressure is within a normal range.

Evidence suggests that dysfunction of CAR leads to overpressure of the brain and pathological injury when arterial blood pressure rises, as for example during exercise. Dysfunction of CAR can also lead to under perfusion of the brain when arterial blood pressure falls, thus causing ischemic injury.

Studies have shown that when the CAR mechanism is dysfunctional, CBF variations exhibit passive, synchronized behavior with respect to steady state arterial blood pressure changes.

There are at least three spontaneous, normally occurring blood pressure variations in the brain, including: 1) variations corresponding to heart rate, 2) variations corresponding to respiration, and 3) nonstationary "slow wave" variations with periods typically over 30 seconds. The first two are relatively cyclic, provided heart rate and respiration rate are constant. The slow wave variations are seldom cyclic with constant period, and their genesis is not well understood.

Spontaneous normally occurring CBF variations include the same three categories as blood pressure. CBF waveforms at heart rate and respiratory frequencies are closely linked to corresponding arterial pressure waveforms. It is Applicant's viewpoint that, CBF slow wave variations are normally not closely linked to blood pressure, and exhibit low coherence to blood pressure in healthy subjects.

It is known to Applicant and others that in addition to the said three types of recurring CBF variations, certain episodic events including visual stimuli and cognitive exertion may produce significant CBF changes without corresponding arterial blood pressure changes.

Other cerebral autoregulatory mechanisms operate independently to adjust cerebral blood flow up or down in response to changes in arterial carbon dioxide and cerebral metabolic needs. Cerebral blood flow therefore varies spontaneously by several percent over time scales corresponding to arterial carbon dioxide fluctuations, which can be 30-120 seconds typically. Spontaneous variations in cerebral blood flow caused by these mechanisms, which are independent of arterial pressure, are therefore not synchronous with, or correlated with, spontaneous arterial pressure fluctuations. These mechanisms confound a straight forward analysis of potential CAR dysfunction.

CBF variations naturally produce synchronized variations in the concentrations of oxy-hemoglobin, deoxy-hemoglobin, and total hemoglobin in a region of tissue. These parameters can be measured noninvasively using near infrared spectroscopy (NIRS). Regional oxygen saturation (rSO2), defined as the ratio of oxy-Hb to total hemoglobin, and other NIRS-derived parameters have been shown to closely correlate with dynamic CBF changes over time scales of interest for CAR assessments The present disclosure is related to methods for evaluation of spontaneous dynamic CBF and arterial pressure changes to determine if the CAR mechanism of a patient is dysfunctional. More specifically, it relates to time-domain measurements of lag time of waveforms of one parameter with respect to the other. The methods described are tolerant of nonstationary variations in the parameters, and therefore do not require stationary data.

BRIEF DESCRIPTION OF THE DRAWINGS

FIG. 11 is a graph showing an example of both blood pressure (first physiological parameter) and cerebral oxygen concentration (second physiological parameter) measurements over a period of time as may be monitored and displayed by the system illustrated in FIG. 1.

DETAILED DESCRIPTION

Figure 1A:
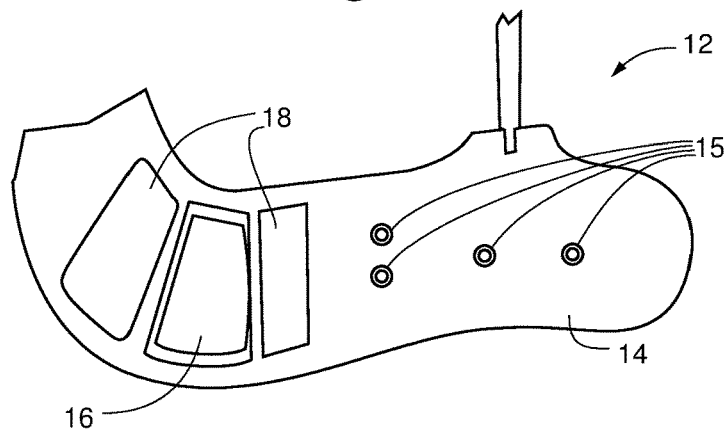
FIG. 1a is a detailed view of the sensor array portion of the system shown in FIG. 1.
Figure 1:
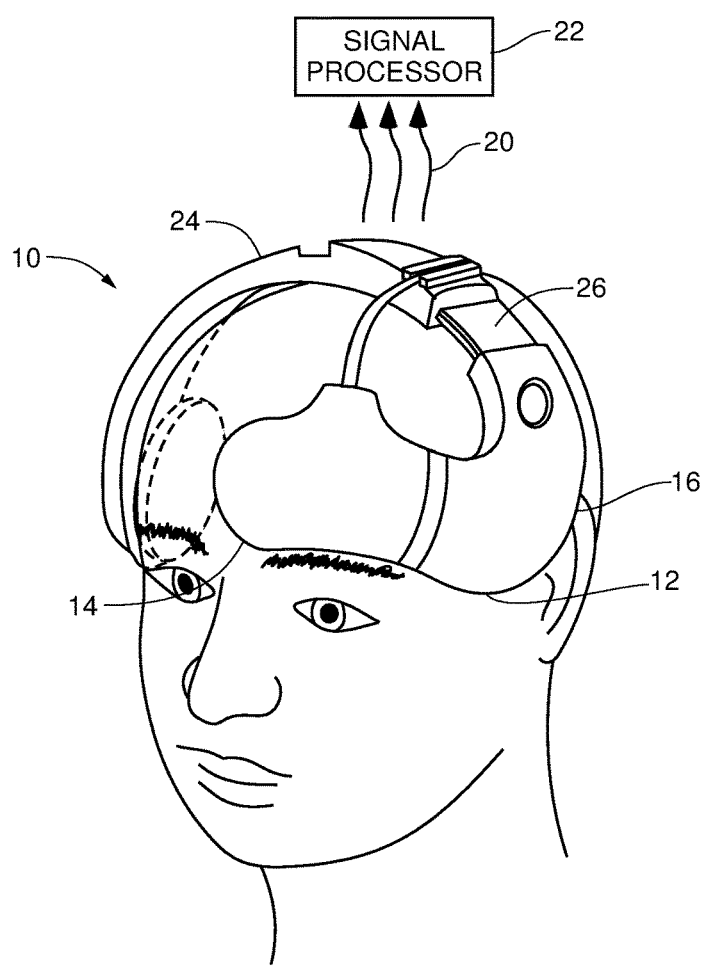
FIG. 1 is a depiction of an embodiment of the system shown in an environment of use.
Figure 2:
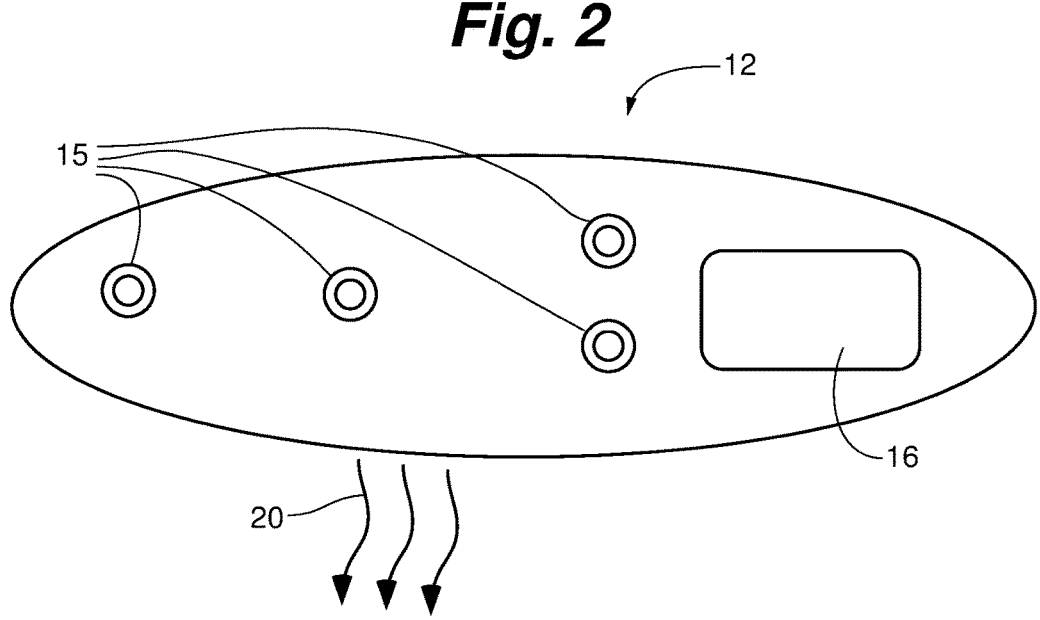
FIG. 2 is a detailed view of a sensor array suitable for use in the embodiment shown in FIG. 1.

As indicated above, embodiments of the disclosure are directed to CAR monitoring and diagnostic systems, methods and devices. An example of one such system 10 is illustrated in FIG. 1. As presented here, the system includes a sensor array 12. The sensor array 12, an example of which is shown in detail in FIGS. 1a and 2 is comprised of: near infrared spectroscopy (NIRS) oximetry elements 14 for optical emission and detection of optical signals; an applanation tonometry pressure sensing device 16; a sensor patch 18 of compliant material that contains the NIRS sensor 14 and applanation tonometry pressure sensor 16 in a desired geometric configuration; a mechanism for digitization, pre-amplification, and prefiltering of the NIRS and pressure signals; and a mechanism of data transmission of the signals (cable, BLUETOOTH® transmitter, etc.) 20 to a signal processing member 22. Applanation tonometry measures relative blood pressure changes, such that pressure waveform morphology and lead time relationships can be calculated.

In addition to the sensor array, the embodiment shown in FIG. 1 includes a headset frame 24 to which the sensor array 12 is mounted. In this embodiment shown in FIG. 1 aspects of the sensor array are mounted at selected points on the headset. For example, the NIRS oximetry sensing member 14 is firmly appositioned to the forehead scalp, or other scalp area of the patient. Correct positioning of the NIRS sensor 14 is achieved by tensioning of an adjustable band 26 that serves the purpose of providing a firm headset fit for a range of cranium sizes. The applanation pressure sensing member 16 is positioned between two force-bearing contact pads 18 in order to mechanically isolate the apposition pressure of the applanation sensor 16 from the headset pressure due to the tensioning of the adjustable band 26.

In at least one embodiment, the NIRS sensor 14 with NIRS optical elements 15 and signal amplifiers is mounted in the headset and located over a region of the forehead with a secure apposition of the NIRS sensor 14 to the skin. Separately the applanation tonometry pressure (ATP) sensor 16 is mounted in the same headset 24 such that the ATP sensor 16 is located over a region of the superficial temporal artery for optimal sensitivity of arterial pressure variations.

In some embodiments, the headset 24 includes a feature that may be located in a preferred location relative to an anatomical feature of the test subject. For example, the positioning of the ATP sensor 16 is optimally located over a preferred segment of the superficial temporal artery. In at least one embodiment, the anatomical feature is the tragus, such that the feature of the headset design enables positioning of the ATP sensor 16 near, or in a desired position relative to, the tragus.

In at least one embodiment, the ATP sensor 16 is distinct or separate from the headset 24 so that it may be placed over the radial artery in the wrist of a patient, instead of over the temporal artery.

In at least one embodiment, the ATP sensor 16 is placed over the brachial artery for arterial pressure applanation. Alternately, the pressure sensor 16 may be placed noninvasively over any artery in which pressure variations may be transmitted to the signal processor 22.

Figure 3:
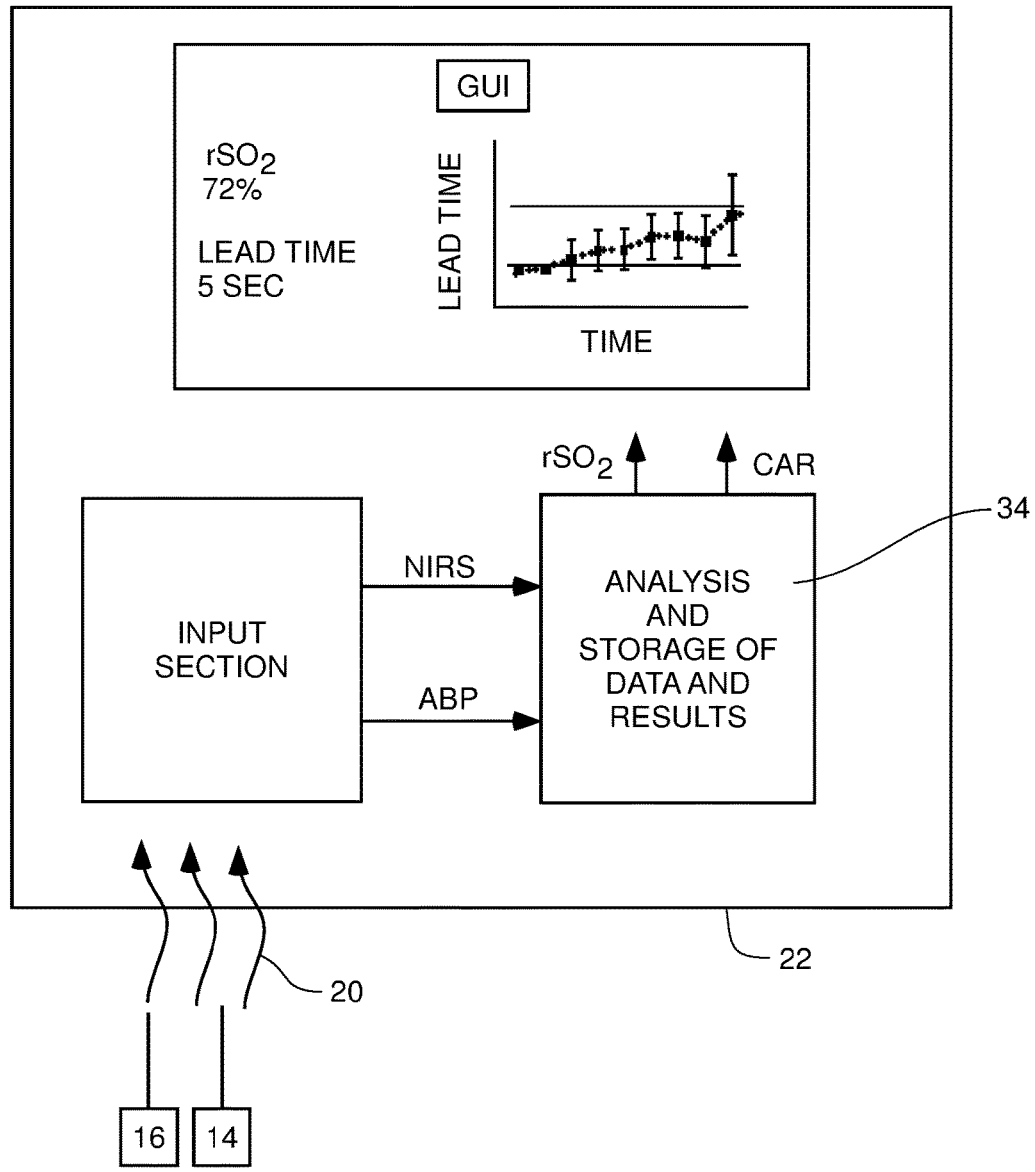
FIG. 3 is a block diagram showing the manner in which the signals received from the sensor of FIG. 2 may be processed by a signal processor.

As is shown in FIG. 3 analysis of the NIRS sensor 14 and pressure sensor 16 data is performed by the signal processing element 22 to determine, among other things, time delays between the parameters, phase differences, and related characteristics of NIRS parameters and blood pressure variations. Results are displayed on the graphical user interphase (GUI) 30.

The signal processing element 22 is in communication with the sensor array 12 by direct (wired) or wireless communication comprised of: an input section 32 capable of receiving wireless data from the NIRS sensor 14 and pressure sensor 16; amplifiers for bandpass filtering and amplification of the applanation blood pressure signal; filtering and pre-conditioning of the optical signal from the NIRS optical detection element; hardware and software 34 for implementing an algorithm for analysis of the NIRS and pressure signals to generate a cross correlation result representative of the lead time between the NIRs and pressure signals; and display of the analysis results in a graphic user interface (GUI) 30 showing numerical and trending data.

In at least one embodiment, the signal processor 22 includes a processing algorithm for analysis of the raw NIRS signals and produces an estimate of the oxy-hemoglobin concentration, deoxy-hemoglobin concentration, total hemoglobin concentration, or other parameter derived from the raw NIRS signals, prior to analysis to generate a cross correlation result.

In at least one embodiment of the invention the sensor array 12 detects and measures two physiological parameters, namely blood pressure (via the ATP sensor or module 16) and cerebral oxygen concentration (via the NIRS sensor 14) over multiple periods of time or episodes. Episodes of interest are identified in the time series of the first parameter, then an assessment is made of the presence and temporal relationships of corresponding episodes in the second parameter.

In some embodiments, the first parameter may be arterial applanation tonometry pressure measured by applanation of an artery. The second parameter may be blood velocity measured in a cerebral artery, or regional cerebral oxygen saturation, as a surrogate for time-varying changes in cerebral blood flow.

In embodiments of the disclosure, the system may be designed, with the use of signal bandpass filtering to, measure time-varying magnitude changes occurring only over relatively long intervals, such as 30-120 seconds or even several minutes; or only over relatively shorter time intervals, such as 3-15 seconds, in order to evaluate physiological effects occurring within a certain range of time scales. Cerebrovascular blood flow autoregulation may be measured with the device by an evaluation of a series of time delays of regional oxygen saturation waveforms relative to arterial applanation tonometry pressure waveforms during episodes of interest in the pressure parameter.

As discussed, the system of FIGS. 1-3 includes a device for measuring cerebral pressure autoregulation by the use of arterial blood pressure and regional cerebral oxygen saturation (first and second parameters). The device detects whether slow arterial blood pressure changes are having an effect on cerebral blood flow, and by this means assesses whether cerebral pressure autoregulation is functional. A continuous measure of arterial pressure is used to track slow blood pressure changes. Regional oxygen saturation is measured to track the cerebral blood flow changes. This substitution is possible because, over the time scales of interest, cerebral blood flow changes are directly reflected in regional cerebral oxygen saturation changes.

Figure 4:
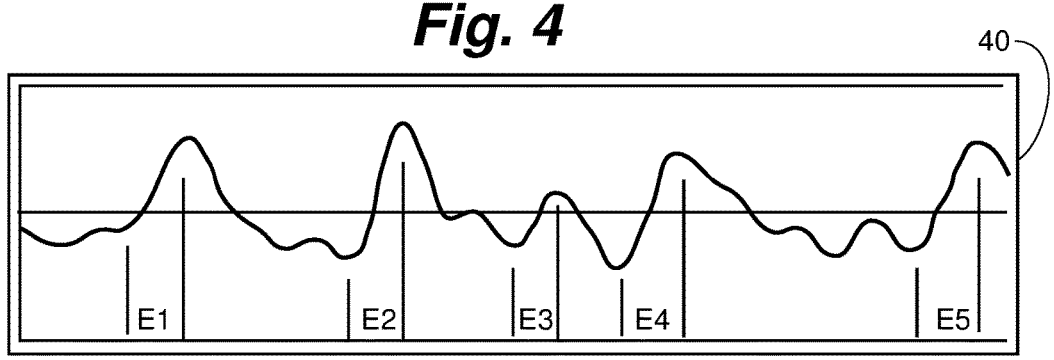
FIG. 4 is a graph showing a first physiological parameter detected and monitored by the system of FIG. 1 over a period of time.
Figure 5:
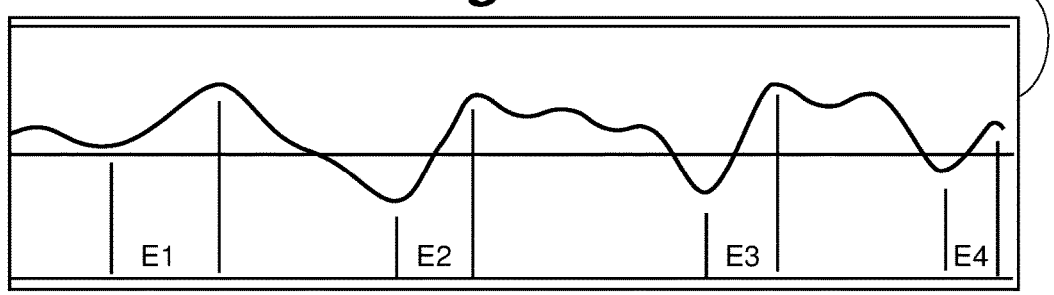
FIG. 5 is a graph showing a second physiological parameter detected and monitored by the system of FIG. 1 over a period of time.

Example time series of monitored first 40 and second 50 physiological parameters are shown in FIGS. 4 and 5 respectively. FIG. 4 depicts a time series of measurements of a first parameter (blood pressure) 40 during a 4-minute episode.

Slow arterial pressure variations are not cyclic changes with a regular frequency, but are highly non-stationary. This is readily seen in the example of FIG. 4. The various devices and approaches described in the prior art for measurement of cerebral pressure autoregulation all lack appreciation for this characteristic. Therefore it is a novel aspect of the present invention that slow arterial pressure variations are each considered as a separate event, with no requirement for stationary cyclic behavior of the parameter.

Figure 6:
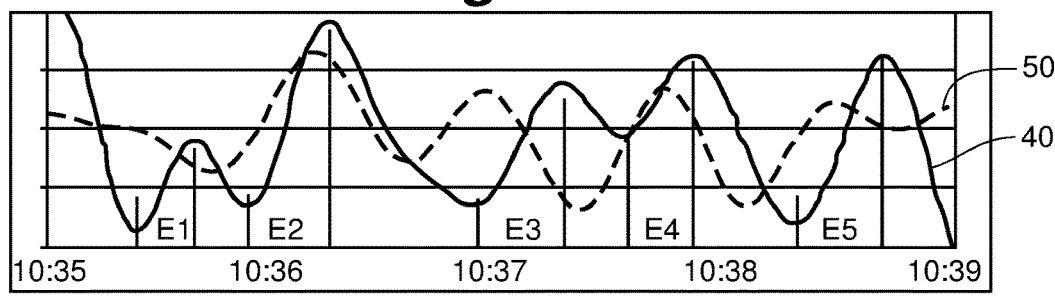
FIG. 6 is a graph showing both a first physiological parameter and a second physiological parameter detected and monitored by the system of FIG. 1 over a period of time and wherein the parameters do not have correspondence with each other.
Figure 7:
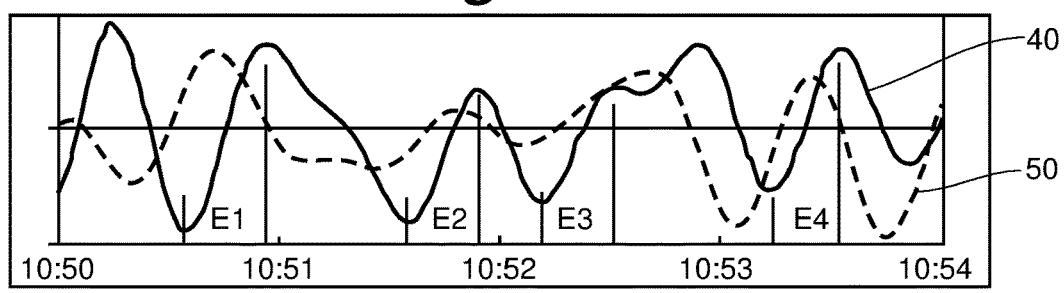
FIG. 7 is a graph showing both a first physiological parameter and a second physiological parameter detected and monitored by the system of FIG. 1 over a period of time and wherein the parameters have correspondence with each other.

In order to measure the effect of arterial blood pressure (ABP) changes 40 on regional cerebral oxygen (rSO2) 50, the system measures the correspondence of rSO2 changes relative to ATP that occur over time scales of 30-120 seconds, such as in the manner shown in FIGS. 6, 7 and 11. ATP and rSO2 time series measurements may be sampled at a higher data rate and then digitally filtered to remove energy outside the bandwidth of 0.008-0.033 Hz, which is not of interest.

A change in ATP is characterized as a waveform which has a beginning at a minimum value, followed by a rising segment during which ATP increases to a maximum value, followed (in some cases) by a maximum plateau, followed by a decreasing segment during which ATP decreases and returns to a minimum value, followed (in some cases) by a baseline segment which precedes the beginning of the next waveform. The rising segment of a waveform is referred to herein as an "episode of interest", which is an ABP response to a neurogenic effect which raises blood pressure. These episodes of interest are identified as E1, E2, etc in FIGS. 4-9.

The time intervals E1-E5 shown in FIG. 4 identify episodes of interest in the first parameter ATP. In this example, an episode of interest is the occurrence of an increasing signal magnitude beginning from a local minimum value and ending at a local maximum value, which includes a zero-crossing or crossing of a threshold value. The episodes of interest have varying temporal characteristics, each corresponding to the rising portion of a waveform.

FIG. 5 shows a time series of measurements of a second parameter of cerebral oxygen or rSO2 during a 3-minute episode. The episodes of interest E1-E4, corresponding to the rising portion of the most significant waveforms, are identified for illustration purposes. In practice the episodes used for evaluation are defined by the episodes of interest in only one parameter, and typically the first parameter.

FIG. 6 shows an example 4-minute time series of both the first and the second parameters over a time interval which includes five episodes of interest (E1-E5) in the first parameter, represented by the solid line. The second parameter, represented by the dashed line, shows no similarity to the first parameter.

FIG. 7 shows an example 4-minute time series of both the first and the second parameters over a time interval which includes four episodes of interest (E1-E4) in the first parameter. In this instance, the second parameter (dashed line) exhibits a significant similarity of pattern to the first parameter.

Figure 8:
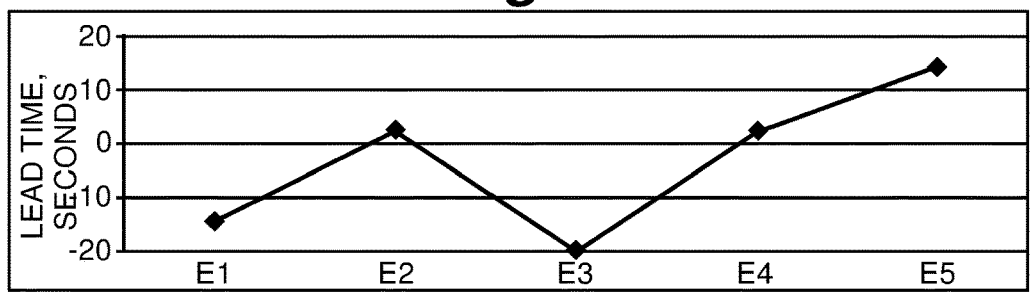
FIG. 8 is a graph showing the measurement of the lead time of the second parameter relative to the first parameter as depicted in FIG. 6.

FIG. 8 shows an example measurement of the lead times of the waveforms of the second parameter relative to the first parameter in FIG. 6, as measured during each of the five episodes of interest. The lead time alternates between large negative and positive values, indicating that the second parameter episodes (or waveforms) are independent of the first parameter.

Figure 9:
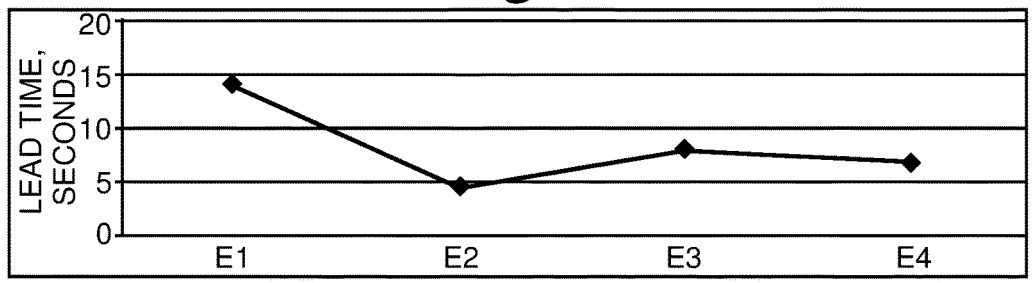
FIG. 9 is a graph showing the measurement of the lead time of the second parameter relative to the first parameter as depicted in FIG. 7.

FIG. 9 shows a measurement of time delays of the waveforms of the second parameter relative to the first parameter in FIG. 7, as measured during the four episodes of interest. In this case the lead times are all within a relatively narrow range of values, indicating a consistent temporal relationship between the second parameter episodes (or waveforms) and those of the first parameter. By visual examination of FIG. 7 it is evident that the second parameter waveforms do indeed show a consistent similarity of pattern in which the episodes of interest (i.e., the rising segments of the waveforms) are time-shifted to the left relative to the first parameter episodes of interest.

The rSO2 (second parameter) changes depicted on the Examples of FIGS. 5-9 are also characterized as waveforms which have the same basic segments. The rSO2 waveforms may not have a similar morphology to that of the ABP (first parameter) waveforms. A typical difference is illustrated by comparison of FIGS. 4 and 5. Slow rSO2 waveforms may be the result of cerebral blood flow responses to arterial carbon dioxide or cerebral metabolic processes, as noted above, or they may be caused by a failure of the cerebral pressure autoregulation (i.e., CAR) mechanisms to adjust cerebrovascular resistance in order to minimize the effects of arterial pressure on cerebral blood flow.

System of FIGS. 1-3 measures the contributory effect of ABP as a cause of rSO2 changes by evaluating the correspondence of episodes of interest (i.e., the rising segments) of rSO2 waveforms relative to contemporaneous ATP waveforms. Absence of rSO2 waveforms indicates no effect of ABP variations on rSO2, and therefore intact CAR. In the presence of rSO2 waveforms, a lack of correspondence indicates that the rSO2 changes, or waveforms, are the result of other effects, and therefore that CAR is functional. Close correspondence between the episodes of interest in the two sets of waveforms indicates that the rSO2 changes are correlated with ABP, and therefore that cerebral pressure autoregulation is not fully functional.

Correspondence is evaluated by measuring the lead time of the rSO2 (second parameter) versus ATP (first parameter) episodes of interest for each of a series of ATP waveforms, such as is depicted in FIGS. 8 and 9. In practice the lead times may be either positive or negative. Consecutive small or zero lead times over a series of waveforms shows a high degree of correspondence, whereas large lead time variability shows lack of correspondence.

Referring to the figures, episodes of interest are first identified in a series of ATP and rSO2 waveforms, as illustrated in FIGS. 4 and 5. For each ATP waveform, a measurement is made of the average lead time of the most contemporaneous rSO2 waveform during the ATP episode of interest.

FIG. 6 illustrates a series of ATP and rSO2 waveforms which do not show correspondence with each other. FIG. 7 illustrates a series of ATP and rSO2 waveforms that show correspondence, in which a rSO2 (dashed line) waveform lead time is evident.

FIG. 8 is an example of a device output for the waveforms shown in FIG. 6. The rSO2 lead times vary from −20 to +15 seconds, confirming a lack of correspondence which is visually evident in FIG. 6. The interpretation of the device output would be that cerebral pressure autoregulation is healthy and functional.

FIG. 9 shows the device output for the waveforms shown in FIG. 7, in which the last three rSO2 lead times are consistently between 5 and 10 seconds. This is evidence of a corresponding effect of ABP on rSO2 changes, and absence of cerebrovascular resistance adjustments. The interpretation of the device output would be dysfunction of cerebral pressure autoregulation.

Analysis and comparison of the monitored parameters may be accomplished in a variety of ways and mechanisms by the signal processor (see FIG. 3). In some embodiments, the digitized NIRS and pressure signals are bandpass filtered by the signal processor to remove signal frequencies outside the range of interest. As indicated above, the frequency range of interest may be 0.008 Hz to 0.033 Hz; alternative higher frequency ranges may also be used for analysis, including 0.008-0.06 Hz, or other bandwidth.

In some embodiments, an initial analysis of the slow wave features of either the NIRS or ATP signals is made to determine an optimal frequency range of interest. For example, Fourier analysis may be made to determine whether a significant proportion of the low frequency power is between 0.03 and 0.06 Hz. Alternatively, an analysis of the wavelengths of slow waves may be made to determine whether a significant proportion of slow waves occur with wavelengths from 16-33 seconds. From this initial analysis, a frequency range of interest for bandpass filtering and lead time calculations may be chosen.

In at least one embodiment, the signal filtering is performed using a Kaiser-Bessel filter whose coefficients have been selected to produce a zero phase shift.

In at least one embodiment, calculation of the lead time relationship between the bandpass filtered NIRS parameter and ATP signal is performed for each discrete pressure waveform in a time series of the data by generating a cross correlation function (CCF) based on a predetermined portion of the ATP waveform and the corresponding NIRS waveform as defined above. In such an embodiment, the time delay $n\tau$ corresponding to the maximum value of the cross correlation function $f(n)$, in which $\tau$ is the time interval between successive digitized data points, is interpreted to represent a real-time estimate of the time delay between the two filtered signals.

In some embodiments, a phase delay is calculated in degrees as the ratio of $n\tau$ divided by the wavelength of the ATP waveform, multiplied by 360 degrees.

Figure 10:
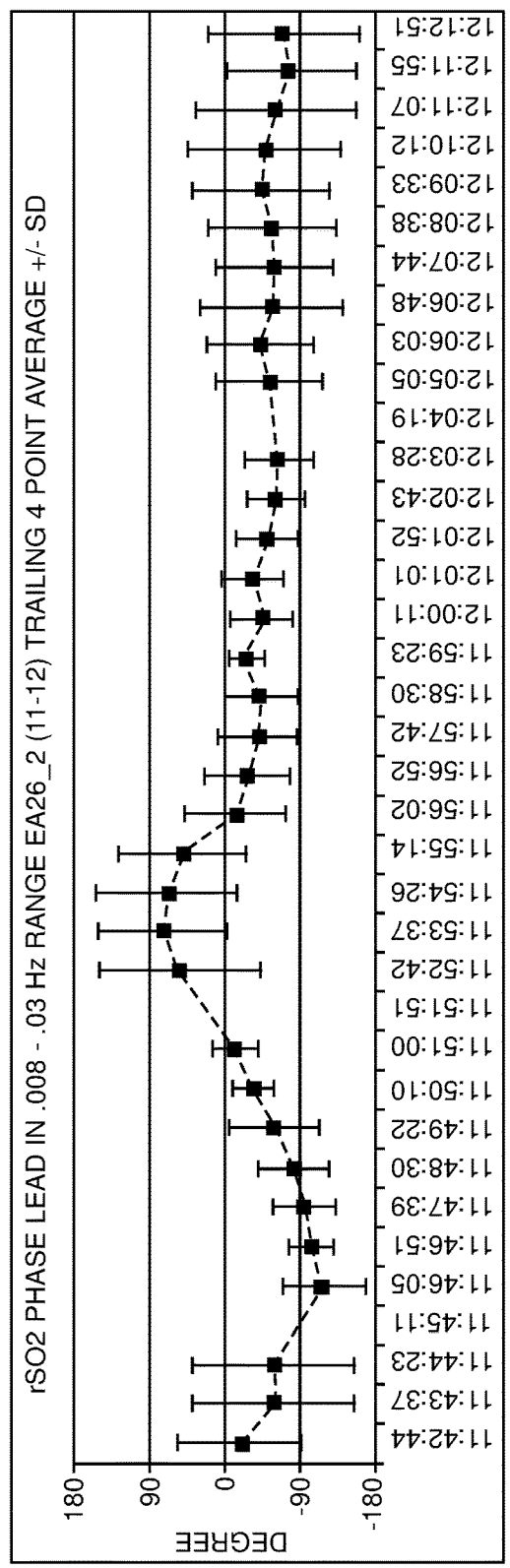
FIG. 10 is a graph showing the lead time of example measurement of cerebral oxygen concentration (second physiological parameter).

In another embodiment, the lead time relationship for each discrete pressure waveform within a selected recent epoch of time (the "phase history"), as illustrated in FIGS. 8, 9 and 10, may be displayed in the GUI as shown in FIG. 3. In a related embodiment, calculation of the phase relationship is performed for each discrete NIRS waveform, instead of each discrete pressure waveform, in a time series of the data.

In some embodiments, the lead time relationships within the selected epoch may be further analyzed with statistical methods to determine a trend; characterize variability (e.g., calculate standard deviation); calculate a mean lead time relationship; estimate the probability that the mean lead time is greater or less than a predetermined lead time, which may be defined as a critical or threshold value; or calculate a confidence interval defining a range within which the mean lead time likely occurs. One or more of these outputs may be used to characterize the extent to which NIRS fluctuating values are passively dependent on pressure variations, as an index of CAR dysfunction.

In another embodiment, the analysis may be performed only on ATP waveforms that meet certain criteria. Alternatively, the analysis may be performed only when NIRS waveforms meet certain criteria, or only when both the ATP and corresponding NIRS waveforms respectively meet certain criteria. For example, exclusion criteria may include low amplitude, high amplitude, presence of artifact (e.g., motion artifact), large difference in wavelength relative to the wavelength of one or more previous waveforms, or large difference in wavelength between the pressure waveform and corresponding NIRS waveform.

In at least one embodiment, the ATP sensing module and headset include structural features that prevent transfer of the headset tension to the applanation pressure sensing member. The structural features may include force bearing members on opposite sides of the ATP sensing member, combined with a constant force device within the ATP sensing module that applies a constant contact force for the ATP sensing member against the skin. A constant force device may include a spring loading, a pressurized bladder, or other device.

Example Process

In at least one embodiment, a measurement procedure may be performed in the following steps:

First, place the headset which includes the NIRS sensing module and the ATP sensing module on the subject to be tested, with the NIRS sensor located over the forehead and the ATP sensing member positioned over a segment of the temporal artery. Fixation is facilitated by a member of the headset extending over the top of the head which has a means of adjusting the tension.

Second, verify that the NIRS and pressure signals are free of artifacts that may result from poor placement technique, and adjust placement of the sensors as necessary.

Third, assure that the surroundings are suitable for stable measurements, and in particular remove noise and other cognitive distractions, while making the patient comfortable.

Next, begin data acquisition and analysis. In this part of the procedure, the signal processor receives the digitized data from the two sensors, and then applies bandpass filtering to successive overlapping epochs of data from each sensor. Ideally the epochs will be sufficiently long to include at least two of the lowest frequency waveforms within the passband (i.e., at least two wavelengths). For example, if the passband is 0.008-0.03 Hz, the filtered epoch may be 2/0.008=250 seconds or more.

Next, the signal processor identifies the time of the beginning of the pressure rise in a first selected waveform ($T_{p,min}$), and also the time of the peak pressure in the first selected waveform ($T_{p,max}$).

Next, the signal processor calculates a non-normalized cross correlation function (CCF), defined as the sum of the products of the ATP values and time-delayed NIRS values over the interval from $T_{p,min}$ to $T_{p,max}$ for each of the predetermined time delay ($n\tau$) values. Therefore, for the first pressure waveform, $$CCF = f(n) = \Sigma P(t) * NIRS(t+n)$$

Where $\tau$ is the sampling interval (i.e., 1/sample rate), and $f(n)$ is calculated over the time interval from $t=T_{p,min}$ to $T_{p,max}$ and over a predetermined range of n that is sufficient to capture a maximum value of $f(n)$ (typically the maximum $n\tau$ is about one half the wavelength of the pressure waveform, and $f(n)$ is calculated for both positive and negative n values). See FIG. 11. In at least some embodiments each of the two waveforms is normalized to a range of −1 to +1 prior to calculation of the CCF, and this normalization is performed separately for each successive waveform pair.

Next the signal processor determines the value of $n\tau$ for which $f(n)$ is maximum, $\tau \cdot n_{CCF\ max}$. This represents the calculated time delay of the NIRS waveform relative to the pressure waveform. The value of $n_{CCFmax}$ may be negative or positive.

Next the signal processor identifies the time of the beginning of the pressure rise from its minimum level, $T_{p,min}$ for the next waveform. The time interval between the two minima is defined as the wavelength $\lambda$ of the first pressure waveform.

Next the signal processor calculates a phase angle φ in degrees using the calculated $\tau \cdot n_{CCF\ max}$ and the calculated wavelength, λ, as follows:

$$\phi = (\tau \cdot n_{CCF\ max}/\lambda) * 360$$

Next the signal processor updates the GUI with the numerical and graphical representation of the phase angle.

Next, after sufficient acquisition of new data, the signal processor applies bandpass filtering to a new epoch of data overlapping with the first epoch, and sufficiently long to include at least the next waveform. Then using the $T_{p,min}$ already determined for the next waveform, the steps of determining $T_{p,max}$ and calculating the CCF, $\tau \cdot n_{CCF\ max}$, λ, and φ will be repeated, and the GUI will be updated.

These steps will continue to repeat until a satisfactory characterization of the behavior of the lead time or phase angle φ can be made. For example, a stable, small lead time may provide a confident assessment within a few wavelengths of time, whereas a variable lead time may require a longer time for an assessment and characterization with acceptable confidence intervals.

In some embodiments, the signal processing member may include several frequency passbands; software for analysis of the relative phase delay between the NIRS and pressure parameters within each passband; an algorithm for determining the frequency dependence of the phase delay; and an algorithm for calculating a maximum, minimum, or optimum coherence and phase delay between the two parameters.

In some embodiments, the signal processing member may include an algorithm and software for determining the signal power or wavelengths in bandpass-filtered NIRS and pressure parameters over a predetermined time interval. The predetermined time interval may be 5 minutes, or any other duration that is longer than $2 \div f_m$ where $f_m$ is the minimum frequency within the frequency bandpass range. The algorithm and software may include a calculation of signal quality based on the signal power of either parameter. The algorithm and software may further use the signal quality calculation to determine a level of confidence in other calculated parameters.

In another embodiment, a CAR assessment protocol includes cognitive stress to provoke a cerebral metabolic change while NIRS and pressure data are acquired. Cognitive stress may be induced by working memory tasks, problem solving, or other method. Lead time calculations prior to and after the stress challenge may be compared for use as an index of dysfunction.

In another embodiment, a CAR assessment protocol includes physical exertion to introduce a cardio-respiratory challenge and a cerebrovascular response while NIRS and pressure data are acquired. Physical exertion may be induced by isometric exercise, aerobic exercise, or other physical activity.

In another embodiment, two or more NIRS sensing members may be used. The sensing members may be placed bilaterally on the forehead and temporal regions. Alternatively, the sensing members may be placed on two or more scalp locations that are located over different regions of the brain, with the single ATP sensing member placed over the temporal artery, radial artery, or other artery. For example, one NIRS sensing member may be placed on or near a location of contusion which is associated with a concussive injury, and another NIRS sensing member may be placed ipsilaterally or contralaterally over a different region of the brain. The signal processing member may include software that compares the results from the sensing members. A local CAR dysfunction may be assessed on the basis of, for example, sufficiently large differences in analysis results between the two locations. A global CAR dysfunction may be assessed on the basis of similar CAR dysfunction indexes obtained at two or more locations.

In another embodiment, a test protocol includes first having the subject breathe normally for a first time interval, preferably at a regular constant respiration rate, for a predetermined duration while NIRS and pressure data are acquired and analyzed as described above, which may be 5 minutes or other duration. After some elapsed time, the subject may breathe normally for a second time interval, preferably at a regular constant respiration rate, for a predetermined duration while NIRS and pressure data are acquired and analyzed as described above. The elapsed time may be 15 minutes, 30 minutes, or other time. This procedure may be repeated for an extended time or number of time intervals as may be desired for dysfunction assessment. An additional assessment protocol is then performed by the software in the signal processing member to calculate a level of dysfunction on the basis of one or more of the lead time assessments performed in the sequence of time intervals.

In some embodiments, the test subject may follow a pattern of activity while NIRS and pressure data are acquired, that may include normal daily routines, physical exertion, cognitive exertion, reading, eating, sleeping, or other activities. In this embodiment the test subject's respiration rate may not be regular, but may vary according to what is a comfortable rate during each activity. The assessment protocol may include an algorithm and software that selects optimum epochs for CAR assessment. Selection criteria for optimum epochs include: absence of apparent artifacts; stable pressure and NIRS waveform amplitudes; or other criteria.

In some embodiments, the input section of the signal processing member includes a means of entering event markers that may be used to identify activities of interest in order to facilitate analysis of test results. Activities of interest may include physical exertion, cognitive exertion, hyperventilation, onset of neuropsychological symptoms, heightened stress response to external stimuli, or other stimulus.

In another embodiment, the signal processing member includes a means of communicating the test results to an external device. The external device may be a smartphone, tablet computer, or other handheld device. Communication to the external device may be either via a cable, such as a USB cable, or via a wireless protocol, such as Bluetooth. The external device may include a means of communicating current test results, historical test results, test subject identification and information, and related data to a remote computer or server using an available communications protocol such as Internet Protocol, File Transfer Protocol, or other internet or telecommunication protocols.

In at least one embodiment, a device such as a smartphone or tablet computer comprises at least a portion of the signal processing member and performs at least some of the functions of the signal processing member.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A system for detecting and diagnosing potential dysfunction of cerebral autoregulation (CAR) comprising:
a headset, the headset containing:
an oximetry sensor, the oximetry sensor configured to detect and measure cerebral oxygen concentration and provide cerebral oxygen concentration measurements over a period of time in the form of cerebral oxygen concentration signals; and
a pressure sensor, the pressure sensor configured to detect and measure arterial blood pressure and provide arterial blood pressure measurements over the period of time in the form of arterial blood pressure signals,
the headset is configured such that when placed on a patient's head the oximetry sensor is positioned over the patient's forehead and the pressure sensor is positioned over a region of the patient's head corresponding to the location of the patient's superficial temporal artery;
the headset in communication with:
a signal processor, the signal processor configured to receive cerebral oxygen concentration signals and arterial blood pressure signals and generate a cross-correlation result representative of lead time between the cerebral oxygen concentration signals and the arterial blood pressure signals; to identify and define a cerebral oxygen concentration waveform based on the cerebral oxygen concentration signals and an arterial blood pressure waveform based on the arterial blood pressure signals, wherein each waveform comprises a beginning minimum value, a rising segment, a maximum value and a decreasing segment, the rising segment being an episode of interest; and to determine a dysfunction of CAR when the cross-correlation result indicates a similarity of pattern between episodes of interest in the waveforms; and
a display, the display configured to display the cerebral oxygen concentration waveform and the arterial blood pressure waveform, the display also configured to display the cross-correlation result and the dysfunction of CAR.

2. The system of claim 1, wherein normal CAR function is displayed when the cross-correlation result indicates no similarity of pattern between episodes of interest in the waveforms.

3. The system of claim 2 wherein the cross-correlation function is defined as the sum of the products of the pressure measurements and time delayed oximetry measurements over a period corresponding to each episode of interest.

4. The system of claim 2 wherein the oximetry sensor comprises an array of near infrared spectroscopy optical elements.

5. The system of claim 2 wherein the pressure sensor comprises an applanation tonometry pressure sensor.

6. The system of claim 2 wherein the oximetry sensor and the pressure sensor are in wireless communication with the signal processor.

7. The system of claim 2 wherein the signal processor comprises at least one bandpass filter through which at least one of the cerebral oxygen concentration signals and arterial blood pressure signals are passed before the signal processor generates the cross-correlation result.

8. A system for detecting dysfunction of cerebral autoregulation (CAR) comprising:
a headset, the headset containing:
an oximetry sensor, the oximetry sensor configured to detect and measure cerebral oxygen concentration and provide cerebral oxygen concentration measurements over a period of time in the form of cerebral oxygen concentration signals; and
a pressure sensor, the pressure sensor configured to detect and measure arterial blood pressure and provide arterial blood pressure measurements over the period of time in the form of arterial blood pressure signals,
the headset is configured such that when placed on a patient's head the oximetry sensor is positioned over the patient's forehead and the pressure sensor is positioned over a region of the patient's head corresponding to the location of the patient's superficial temporal artery;
the headset in communication with:
a signal processor, the signal processor configured to receive cerebral oxygen concentration signals and arterial blood pressure signals, identify and define a series of Episodes of Interest (EOI) in a series of arterial blood pressure signal waveforms, each waveform comprising a beginning minimum value, a rising segment, a maximum value and a decreasing segment, the rising segment being an EOI, and for each EOI generate a result representative of lead time between the cerebral oxygen concentration signal and the arterial blood pressure signal to produce a series of EOI lead time results; and
a display, the display configured to display the series of EOI lead time results during the measurement period of time.

9. The system of claim 8, wherein the EOI lead time results are determined using a cross correlation function over each separate EOI to obtain optimal lead time estimates for each of the EOIs.

10. The system of claim 8, wherein the series of EOI lead times is determined by calculating the lead time between the beginning minimum value of the arterial blood pressure EOI and the beginning minimum value of the closest cerebral oxygen EOI.

* * * * *